(12) United States Patent
Zaniboni et al.

(10) Patent No.: US 12,343,465 B2
(45) Date of Patent: Jul. 1, 2025

(54) PURGER DEVICE FOR OXYGENATORS

(71) Applicant: Sorin Group Italia S.r.l., Milan (IT)

(72) Inventors: Andrea Zaniboni, San Martino Spino (IT); Claudio Silvestri, Quarantoli Mirandola (IT)

(73) Assignee: Sorin Group Italia S.r.l., Milan (IT)

( * ) Notice: Subject to any disclaimer, the term of this patent is extended or adjusted under 35 U.S.C. 154(b) by 806 days.

(21) Appl. No.: 17/675,044

(22) Filed: Feb. 18, 2022

(65) Prior Publication Data

US 2022/0168483 A1 Jun. 2, 2022

Related U.S. Application Data

(63) Continuation of application No. PCT/IB2019/057484, filed on Sep. 5, 2019.

(51) Int. Cl.
*A61M 1/16* (2006.01)
*A61M 1/36* (2006.01)

(52) U.S. Cl.
CPC ........ *A61M 1/1698* (2013.01); *A61M 1/1601* (2014.02); *A61M 1/1627* (2014.02); *A61M 1/3638* (2014.02); *A61M 2205/3331* (2013.01); *A61M 2205/7554* (2013.01)

(58) Field of Classification Search
CPC . A61M 1/1698; A61M 1/1601; A61M 1/3638
See application file for complete search history.

(56) References Cited

U.S. PATENT DOCUMENTS

2010/0101657 A1   4/2010   Morley et al.

FOREIGN PATENT DOCUMENTS

| DE | 19820158 A1 | 11/1999 |
| EP | 3056233 A1 | 8/2016 |

OTHER PUBLICATIONS

International Search Report and Written Opinion dated Apr. 29, 2020 for International Application No. PCT/IB2019/057484.

*Primary Examiner* — Leslie R Deak
(74) *Attorney, Agent, or Firm* — Seager, Tufte & Wickhem LLP (57) ABSTRACT

A purger device for hollow fiber oxygenators, including a gas inlet, a gas outlet, and a fluid communication feature between the gas inlet and the gas outlet. The purger device further including an accumulation chamber having a variable volume plenum ported to the fluid communication feature, and a flow control unit configured to vary fluid communication patterns in the fluid communication feature and having a first operating condition and a second operating condition, wherein in the first operating condition the flow control unit enables a fluid communication between the gas inlet and gas outlet, and wherein in the second operating condition the flow control unit enables a fluid communication between the gas inlet and the variable volume plenum of the accumulation chamber.

34 Claims, 7 Drawing Sheets

PURGER DEVICE FOR OXYGENATORS

CROSS REFERENCE TO RELATED APPLICATIONS

This application is a continuation of International Application No. PCT/IB2019/057484, filed Sep. 5, 2019, the disclosure of which is incorporated herein by reference.

TECHNICAL FIELD

The present disclosure refers to perfusion systems, and more particularly to components therefor.

BACKGROUND

Membrane hollow fiber oxygenators used in perfusion systems supporting blood extracorporeal circulation are subject to condensation of water vapor inside the fiber inner lumens. This phenomenon, known as "wet lung", becomes significant after prolonged blood extracorporeal circulation (or with pediatric oxygenators wherein thin wall fibers are used). The wet lung phenomenon negatively impacts gas exchange and may result in lowered oxygen deli very to the patient and reduced carbon dioxide removed from the patient.

To overcome the wet lung issue, manufacturers instruct perfusionists to manually increase gas flow (if necessary, up to 20 lpm, while the normal flow range is 0 to 10 lpm) for a few seconds in order to flush the oxygenator gas path by pushing the condensed water out of the fiber inner lumens, thus re-establishing a safe gas exchange.

During the flushing, due to the increased flow, gas pressure in the oxygenator may become higher than blood pressure. If this happens, gas may cross the microporous fiber wall and enter the blood path, thus putting the patient at risk of gaseous embolization.

In order to prevent (and avoid) water vapor condensation in the gas exchange hollow fibers, the applicants proposed a solution disclosed in PCT/IB2017/053229, which consists of a specifically designed oxygenator wherein water, before entering the heat exchanger, is circulated through a sort of muff created around the fiber gas outlet end, so as to thermally insulate it from the ambient and avoid temperature drops which would favor water condensation into the fibers.

However, regardless of the effectiveness thereof this solution requires a purposely designed oxygenator, i.e. it is not open to retrofitting on existing oxygenator layouts. In addition to the manufacturing issue, this may be an issue in that medical personnel in charge of perfusion duties may have to be re-trained to use new devices.

SUMMARY

In a first example, a purger device for hollow fiber oxygenators includes a gas inlet, a gas outlet, and a fluid communication feature between said gas inlet and said gas outlet. The purger device further includes an accumulation chamber having a variable volume plenum ported to said fluid communication feature, and a flow control unit configured to vary fluid communication patterns in said fluid communication feature and having a first operating condition and a second operating condition, wherein in the first operating condition the flow control unit enables a fluid communication between said gas inlet and gas outlet, and wherein in the second operating condition the flow control unit enables a fluid communication between said gas inlet and the variable volume plenum of said accumulation chamber.

In a second example according to the first example, wherein in the first operating condition said fluid accumulation chamber is maintained in fluid communication with the gas inlet and the gas outlet.

In a third example according to the first example or the second example, wherein in the second operating condition said gas outlet is excluded from fluid communication between the gas inlet and the variable volume plenum of said accumulation chamber. In a fourth example according to the third example, wherein in the second operating condition of the flow control unit the gas outlet is occluded.

In a fifth example according to the first example, wherein the variable volume plenum of said accumulation chamber is at least partly delimited by an elastic membrane configured for allowing volume expansion of said variable volume plenum when the flow control unit is in the second operating condition.

In a sixth example according to any of the previous examples, wherein said flow control unit is a spool valve including a mobile spool member movable along a portion of said fluid communication feature.

In a seventh example according to the sixth example, wherein the mobile spool member is operable by way of a push button.

In an eighth example according to the seventh example, wherein the push button is biased towards the first operating condition.

In a ninth example according to the sixth example, wherein the mobile spool member is electrically operated.

In a tenth example according to any of examples sixth to ninth, including a main housing comprising a first, inlet, channel having a first axis, the first channel being in fluid communication with the gas inlet, a second channel having a second axis orthogonal to the first axis, and a third, outlet, channel having a third axis orthogonal to the first axis and the second axis, the third channel being in fluid communication with the gas outlet, and wherein the mobile spool member is arranged slidable along the second channel.

In an eleventh example according to the tenth example, wherein the mobile spool member includes a first portion and a second portion separated by an annular groove, wherein in the first operating condition the mobile spool member is positioned such that the annular groove is in view of the first channel and the third channel to allow a fluid flow through the fluid communication feature to bypass the spool member when proceeding from the gas inlet, through the first channel, and out to the gas outlet.

In a twelfth example according to the eleventh example, wherein in the second operating condition the mobile spool member is positioned so that the first portion overlaps with a porting of the first channel onto the second channel and with a porting of the third channel onto the second channel, thereby cutting off fluid communication between the first channel and the third channel.

In a thirteenth example according to any of examples first to sixth, wherein the flow control unit includes a clampable tube providing the gas outlet, and an electrically operated clamp configured to selectively clamp or release the clampable tube.

In a fourteenth example according to the thirteenth example, including a backplate provided with said gas inlet, the backplate being configured for fitting the purger device into a receiving socket of a gas blender.

In a fifteenth example according to the fourteenth example, wherein said backplate also includes a connector member providing a pressure sensing line.

In a sixteenth example according to any of examples first, fourteenth, fifteenth, wherein said gas inlet is in fluid communication with said variable volume plenum of said accumulation chamber.

In a seventeenth example according to the sixteenth example, wherein said connector member providing the pressure sensing line is in fluid communication with said variable volume plenum.

In an eighteenth example according to the sixteenth or seventeenth example, wherein a one-way valve is arranged between said plenum and said backplate.

In a nineteenth example according to any of examples sixteenth to eighteenth, wherein said clampable tube is in fluid communication with said plenum.

In a twentieth example according to any of examples fifth to nineteenth, wherein said membrane is coupled to a gauge pin configured to protrude out of a casing of said purger device by an extent dependent on a deformation of said membrane.

In a twenty-first example according to the twentieth example, wherein said membrane is capped by a dome, the gauge pin being mounted slidable through a hub provided on said dome.

In a twenty-second example, a gas blender for use in a perfusion system, the gas blender comprising a receiving socket and a purger device according to any of examples fourteenth to twenty-first hosted in said receiving socket.

In a twenty-third example according to the twenty-second example, including a blended gas delivery port and a pressure sensing port, and wherein the backplate of said purger device includes a first connector member providing said gas inlet, and a second connector member ported to the fluid communication feature of said purger device, wherein the first connector member is configured to plug into the gas delivery port when the purger device is fitted into the receiving socket, and wherein the second connector member is configured to plug into the pressure sensing port when the purger device is fitted into the receiving socket.

In a twenty-fourth example according the twenty-third example, further including a pressure transducer configured for sensing pressure in the fluid communication feature of the purger device through said pressure sensing port and said second connector member, the pressure transducer being operatively connected to a control unit configured for operating a clamp member to selectively occlude the clampable tube at the gas outlet of the purger device.

In a twenty-fifth example according to the twenty fourth example, wherein the control unit is configured for operating the clamp member to occlude the clampable tube, thereby bringing the flow control unit to the second operating condition and allowing gas to accumulate in the variable volume plenum of the accumulation chamber, when a first threshold pressure is reached or exceeded and sensed by the pressure transducer, the threshold pressure being a threshold backpressure at the gas outlet of the purger device, and operating the clamp member to release the clampable tube, thereby bringing the flow control unit to the first operating condition venting the gas accumulated in the variable plenum of the accumulation chamber through the gas outlet of the purger device, when a second threshold pressure is reached or exceeded, the second threshold pressure being a threshold pressure in said variable volume plenum of the accumulation chamber.

In a twenty-sixth example according to the twenty-fourth example, wherein the control unit is configured for operating the clamp member to occlude the clampable tube, thereby bringing the flow control unit to the second operating condition and allowing gas to the accumulate in the variable volume plenum of the accumulation chamber in response to a manual control initiated by a user, and operating the clamp member to release the clampable tube, thereby bringing the flow control unit to the first operating condition and venting the gas accumulated in the variable volume plenum of the accumulation chamber through the gas outlet of the purger device, when a threshold pressure in said variable volume plenum of the accumulation chamber is reached or exceeded.

In a twenty seventh example according to the twenty fourth example, wherein the control unit is configured for operating the clamp member to occlude the clampable tube, thereby bringing the flow control unit to the second operating condition and allowing gas to accumulate in the variable volume plenum of the accumulation chamber, at a first preset time, and operating the clamp member to release the clampable tube, thereby bringing the flow control unit to the first operating condition and venting the gas accumulated in the variable volume plenum of the accumulation chamber through the gas outlet of the purger device, at a second preset time, the second preset time being later than the first preset time.

In a twenty eighth example, a method of purging gas exchange hollow fibers of a blood oxygenator in a perfusion system by means of a purger device according to any of examples first to twenty-seventh, wherein the gas exchange hollow fibers include inner lumens in fluid communication with an oxygenator gas inlet, wherein the perfusion system includes a gas blender configured to deliver a gas blend to the gas inlet of said purger device, and wherein the gas outlet of the purger device is in fluid communication with the oxygenator gas inlet. The method comprising switching the flow control unit to the second operating condition to accumulate gas from the gas blender in the variable volume plenum of the accumulation chamber, and switching the flow control unit to the first operating condition to release the gas accumulated in the variable volume plenum of the accumulation chamber to the oxygenator gas inlet, thereby flushing the inner lumens of the gas exchange hollow fibers.

In a twenty-ninth example according to the twenty-eighth example, wherein said switching the flow control unit to the second operating condition is performed at a first preset time, and said switching the flow control unit to the first operating conditions is performed at a second preset time, later than the first preset time.

In a thirtieth example according to the twenty-ninth example, further comprising estimating whether an accumulation of condensed water vapor in the inner lumens of the gas exchange hollow fibers exceeds a predetermined threshold, wherein said switching the flow control unit to the second operating condition is performed upon exceeding said predetermined threshold.

In a thirty-first example according to the thirtieth example, wherein said predetermined threshold is a first threshold pressure, the first threshold pressure being a threshold backpressure at the gas outlet of the purger device.

In a thirty-second example according to the thirtieth example, wherein said predetermined threshold is a minimum allowed oxygen deli very threshold to a patient's blood flowing across the gas exchange hollow fibers.

In a thirty-third example according to the thirtieth example, wherein said switching the flow control unit to the first operating condition is performed when gas pressure in the variable volume plenum of the accumulation chamber exceeds a second pressure threshold, the second pressure threshold being a pressure threshold in the variable volume plenum of the accumulation chamber.

In a thirty-fourth example according to any of examples twenty ninth to thirty third, wherein backpressure at the gas outlet) of the purger device and/or gas pressure in the variable volume plenum of the accumulation chamber are fed back to a control unit to respectively adjust the timing of said switching the flow control unit to the second operating condition and/or switching the flow control unit to the first operating condition.

BRIEF DESCRIPTION OF THE DRAWINGS

Further features and advantages of the disclosure will become apparent from the following description with reference to the annexed drawings, given purely by way of non-limiting example, wherein.

DETAILED DESCRIPTION

Figure 1:
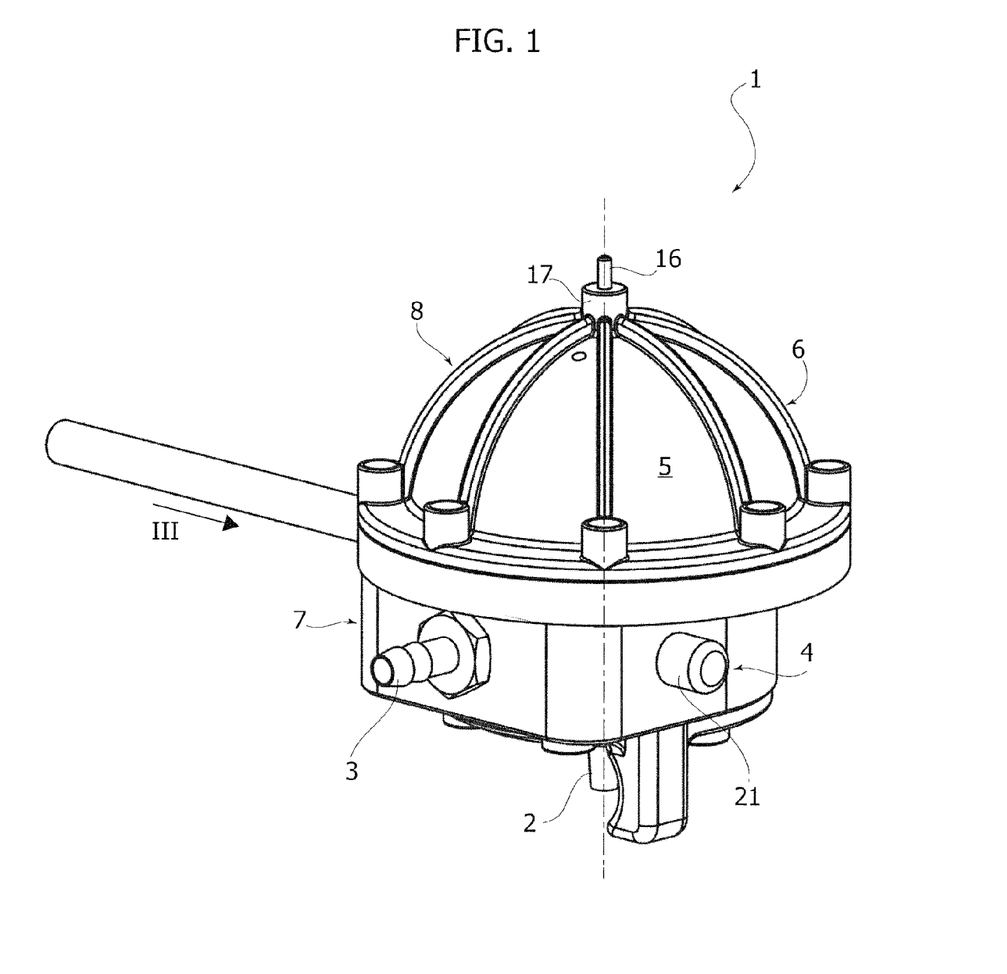
FIG. 1 is a perspective view of a purger device, according to embodiments of the disclosure.
Figure 3:
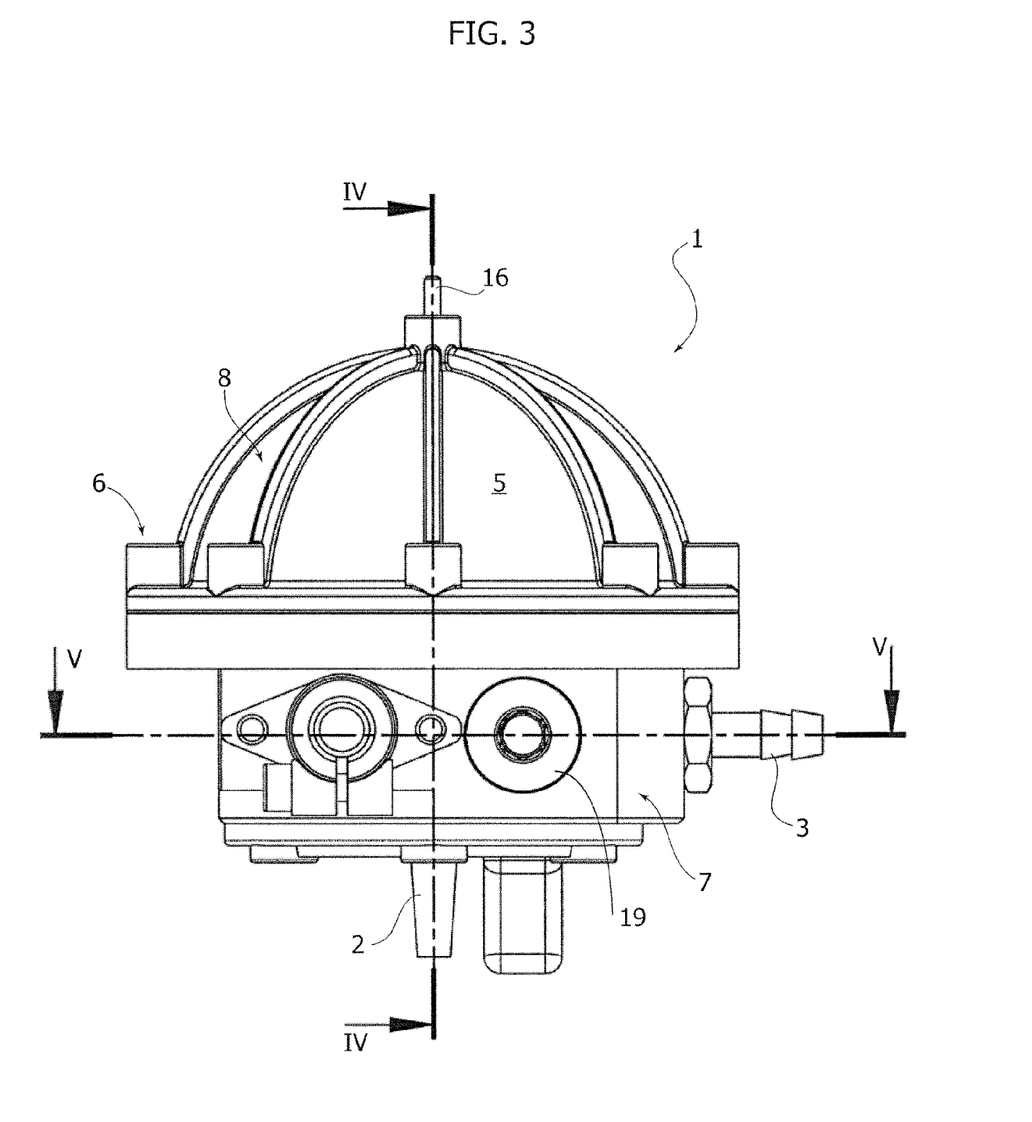
FIG. 3 is an orthogonal view according to arrow III in FIG. 1, according to embodiments of the disclosure.

Reference number 1 throughout the Figures designates as a whole a purger device, according to embodiments of the disclosure. With reference to FIGS. 1 and 3, in embodiments, the purger device 1 includes a gas inlet 2, a gas outlet 3, a fluid communication feature between the gas inlet 2 and the gas outlet 3, a flow control unit configured to vary fluid communication patterns in the fluid communication feature, and an accumulation chamber 5, which is ported to the fluid communication feature so as to be put in fluid communication with the gas inlet 2 and/or the gas outlet 3 depending on the fluid communication pattern established by the flow control unit 4.

In embodiments, the purger device 1 may include a casing 6 comprising a main housing 7 and a dome 8 fastened to the main housing 7.

In embodiments, the main housing 7 hosts the fluid communication feature of the purger device 1, which may be provided as a network of one or more channels provided into and through the main housing 7 to define fluid communication paths between the working ports of the purger device 1 (gas inlet 2, gas outlet 3, and accumulation chamber 5 port) into the main housing 7 and the casing 6.

Figure 2:
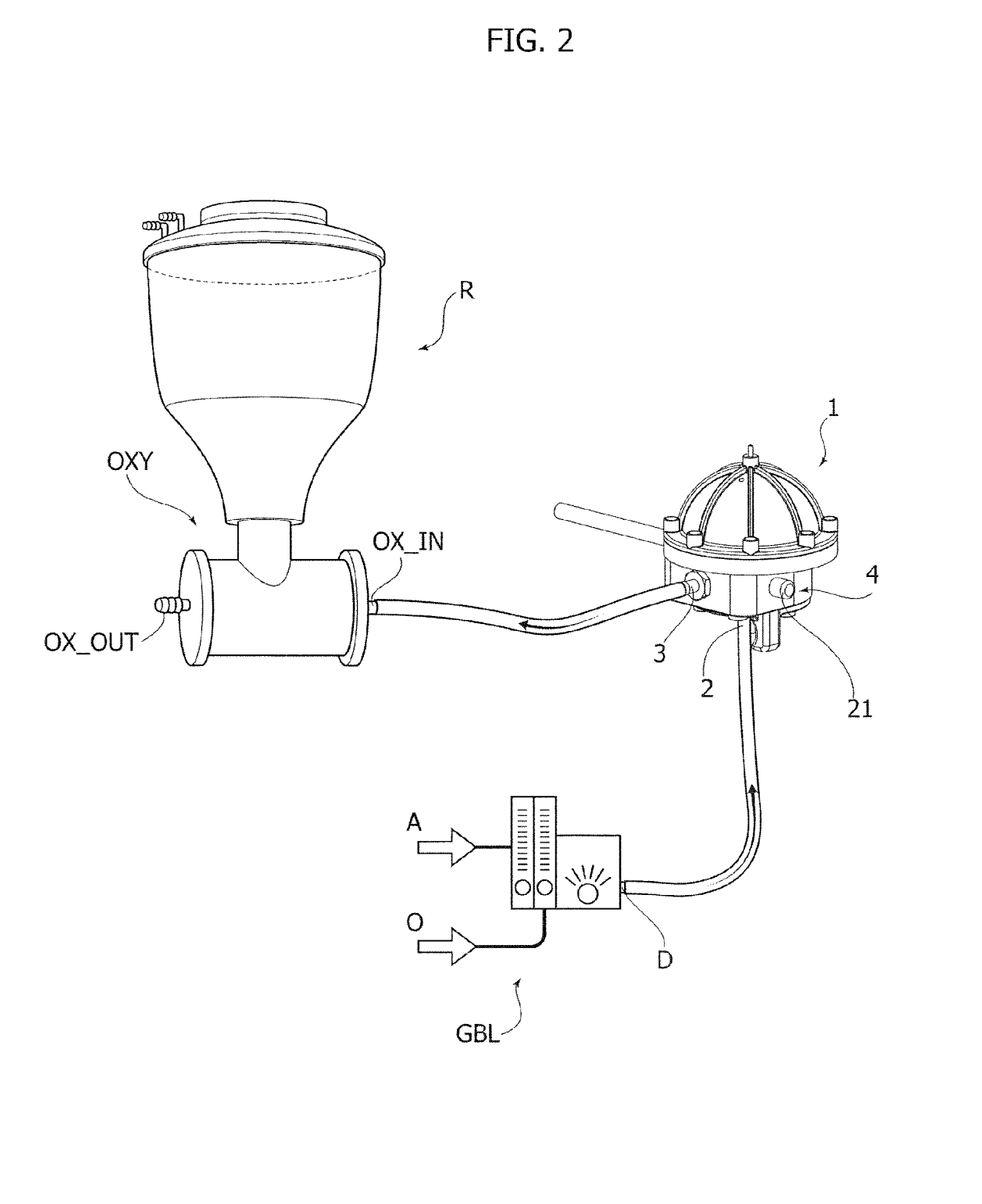
FIG. 2 is a schematic view of the layout of a perfusion system featuring a purger device, according to embodiments of the disclosure.
Figure 4:
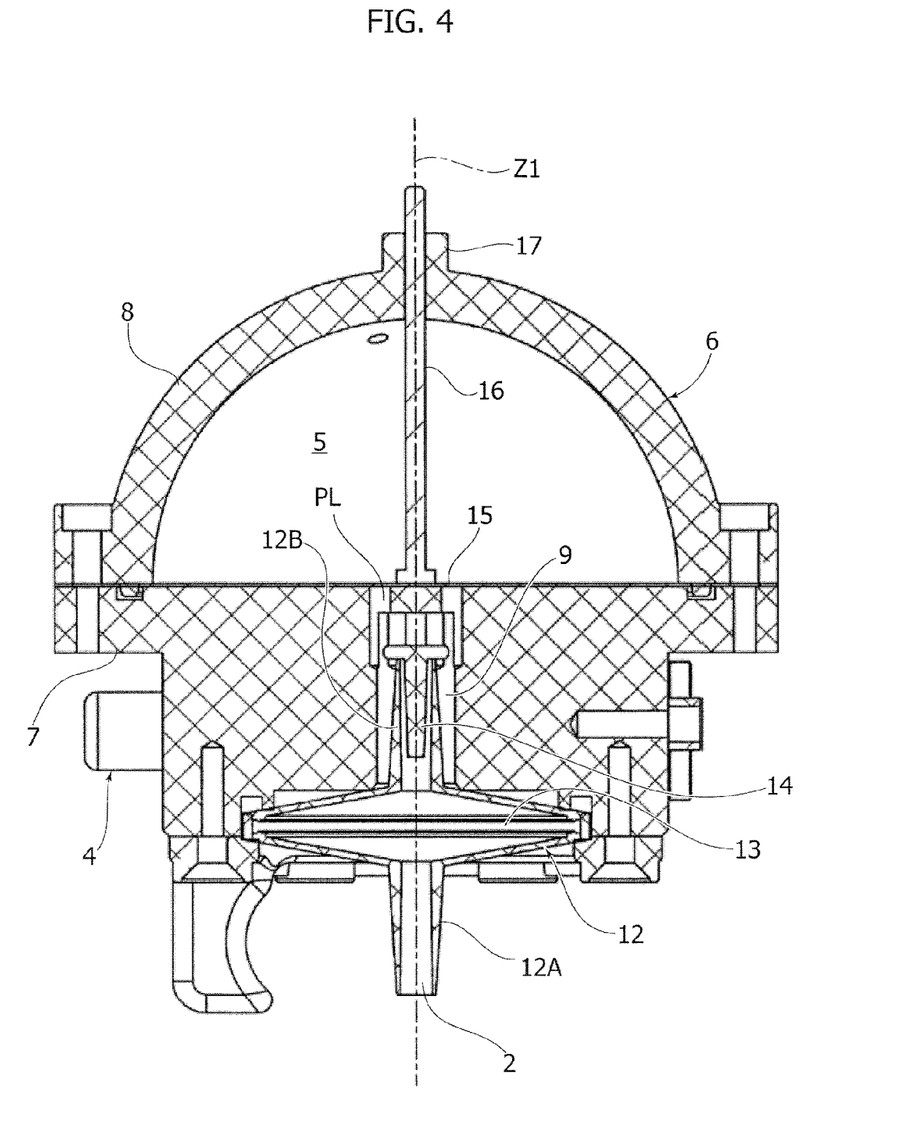
FIG. 4 is a sectional view taken along plane IV-IV in FIG. 3, also representing the fluid communication feature with the purger device in the first operating condition, according to embodiments of the disclosure.
Figure 5:
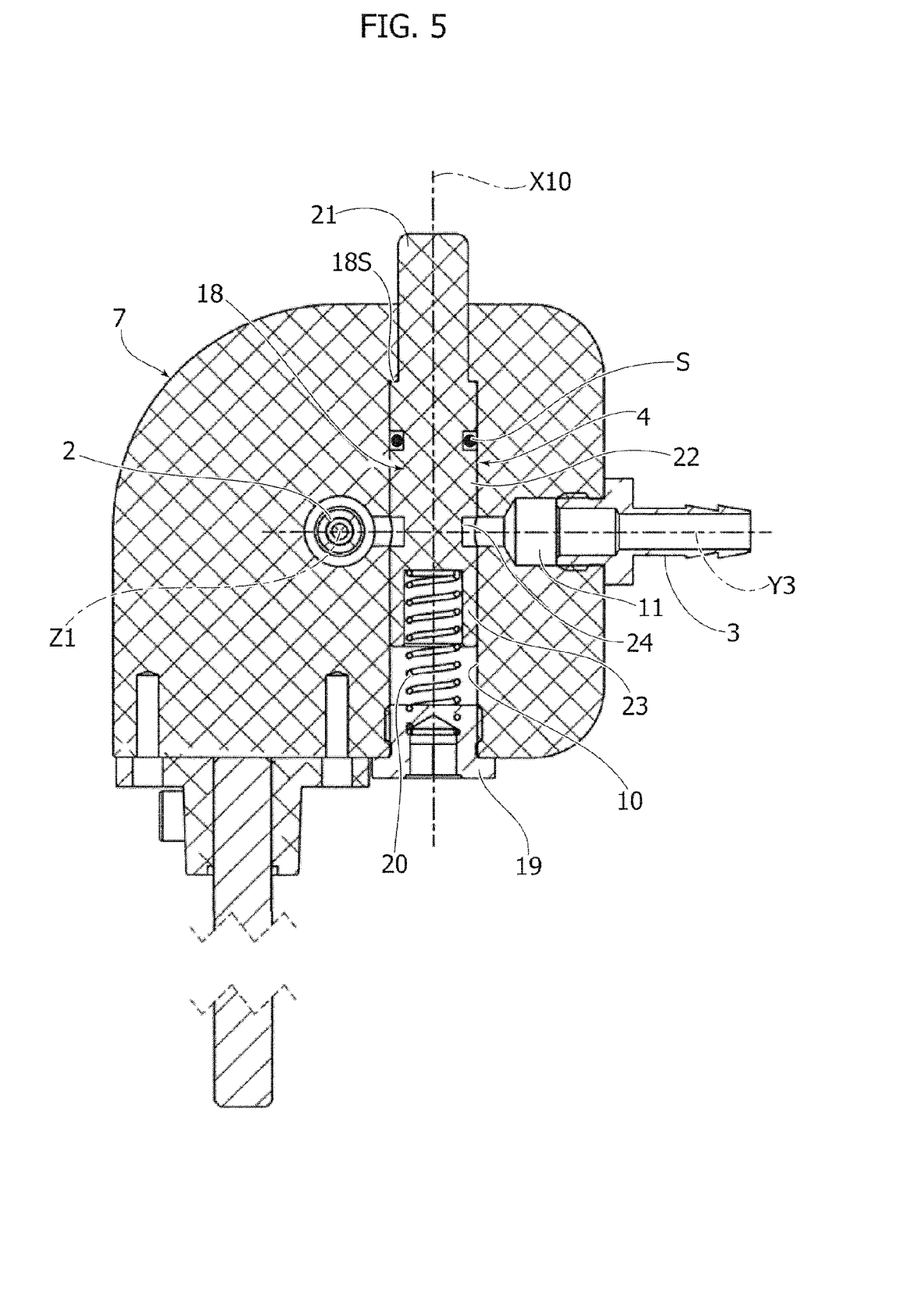
FIG. 5 is a sectional view taken along plane V-V in FIG. 3, also representing the fluid communication feature with the purger device in the first operating condition, according to embodiments of the disclosure.

FIG. 2 shows an exemplary connection layout of the device 1 into a perfusion system including a gas blender GBL and an oxygenator OXY. The oxygenator OXY is itself connected downstream of a blood reservoir R. The gas blender GBL includes an air inlet/supply A and an oxygen inlet/supply O, and is configured to blend air and oxygen (or nitrogen and oxygen wherein the air inlet/supply is replaced by a nitrogen supply) into a delivery flow to the purger device 1, leaving the gas blender through a delivery port D thereof connected to the gas inlet 2. The gas outlet 3 is in turn connected to the gas inlet OX_IN of the oxygenator OXY, the gas inlet being in fluid communication with gas exchange hollow fibers, across which blood from the reservoir R flows. Gas exchange hollow fibers have an inner lumen configured to receive the blended gas supplied by the blender GBL and to exchange the latter with blood flowing across the hollow fiber bundle. An oxygenator gas outlet (or escape) port OX_OUT is open to the atmosphere. With reference to FIGS. 4 and 5, in embodiments, the main housing 7 may include a first, inlet, channel 9 parallel or coaxial to a longitudinal axis Z1 of the purger device 1, a second channel 10 having an axis X10 orthogonal to the axis Z1, and a third, outlet, channel 11 having an axis Y3 orthogonal to both axes X10 and Z1.

In embodiments, the inlet channel 9 may receive a filter assembly 12, which in turn houses a gas filtering element 13. The gas filtering element 13 may for example have a 0.2 μm mesh size to sterilize the gas entering the purger device 1, and may be a screen element hosted in a disc shaped portion of the filter assembly 12. The filter assembly 12 may further include opposite sleeve-like members 12A and 12B providing inlet and outlet ducts of the filtering assembly 12, wherein inlet duct 12A is in fluid communication with (or itself provides) the gas inlet 2, and outlet duct 12B leads out towards the channel 11. In embodiments, the outlet duct 12B may additionally provide a seat for a poppet element 14, which is one-way displaceable under gas flow and pressure from the inlet channel 9.

In embodiments, the accumulation chamber 5 includes a plenum PL, which is an inner volume delimited by inner walls and boundaries of the accumulation chamber 5. The plenum PL is a variable volume plenum owing, in embodiments, to the provision of an elastic membrane 15 which defines one wall thereof (or, more in general, part of the complex of inner walls and boundaries). The variable volume plenum is at least partly delimited by a deformable member (such as the membrane 15) or a displaceable member (e.g. a spring piston, for instance in a cylinder-shaped accumulation chamber), so to accommodate volume variations of the plenum itself.

The membrane 15 is fixed to the casing 6 along a perimeter thereof (e.g. pinched or nipped between the dome 8 and the main housing 7) and includes one side facing the plenum PL which is exposed to the inlet channel 9 downstream of the filter assembly 12, and another—opposite—side exposed to the interior of the dome 8, which is in turn exposed to atmospheric (ambient) pressure. The dome 8 has a substantially hemispherical shape to accommodate the bulging deformation of the membrane 15 when subject to gas pressure and flow from the gas inlet 2 and the inlet channel 9. With the membrane 15, the variable volume plenum PL of the accumulation chamber 5 essentially operates as a pressure/flow accumulator.

In embodiments, the membrane 15 may be advantageously coupled to a gauge pin 16 mounted slidable through a hub 17 provided at the top of the dome 8. The gauge pin 16 provides visual evidence of the membrane deformation, and accordingly the pressure level of the gas in the plenum PL of the chamber 5.

With reference to FIG. 5, in embodiments, the flow control unit 4 may be provided as a spool valve featuring a mobile spool member 18. The mobile spool member 18 is slidable along the channel 10 coaxially to the axis X10, so that functionally the spool valve is provided and housed in same channel 10, which is closed at one end by a plug 19. The plug 19 also provides an axial abutment to a first end of a biasing member 20, for example embodied as a helical spring, the second end of which bears upon the mobile spool member 18 which is sealed by means of an O-ring S. The mobile spool member also bears upon a shoulder 18S in the main housing 7 opposite the plug 19, and protrudes out of the main housing 7 to provide a push button 21. The push button 21 is configured for operation of the mobile spool member 18 along the axis X10.

In embodiments, the mobile spool member 18 include a first portion 22 and a second portion axially separated by an annular groove 24.

In a first operating condition of the spool valve, depicted in both FIGS. 4 and 5, a fluid communication is enabled between the gas inlet 2 and the gas outlet 3 thanks to the annular groove 24: the mobile spool member is positioned in the channel 10 so that the annular groove 24 is in view of the first, inlet, channel 9 and the third, outlet, channel 11 to allow a fluid flow through the fluid communication feature to bypass the spool member 18 when proceeding from the gas inlet 2, through the first channel 9, and out to the gas outlet 3 (via PL and channel 11).

In embodiments, the fluid communication with the plenum PL of the accumulation chamber 5 is not cut off, i.e. the port at which the plenum PL of the accumulation chamber 5 connects with the fluid communication feature of the purger device 1 (here, in particular, the channel 9) is not occluded by either portions 22 or 23 of the spool member 18. Gas is prevented from substantially accumulating in the plenum PL of the chamber 5 by the stiffness of the membrane 15, and flows directly to the gas outlet 3 (where normal working pressures are not high enough to deflect membrane 15).

In some embodiments, the plenum PL of the accumulation chamber may be ported to the fluid communication feature so as to be occluded by a spool 22 or 23 (or other port controlling means, depending on the construction of the flow control unit 4) when the spool valve is in the first condition.

In a second operating condition of the spool valve the spool member 18 is displaced towards the plug against the biasing action of the spring 20, so that the spool 22 occludes the passageway from the inlet channel 9 to the outlet channel 11.

More in detail, in the second operating condition the mobile spool member 18 is positioned so that the first portion 22 overlaps with a porting of the first channel 9 onto the second channel 10 and with a porting of the third channel 11 onto the second channel 10, thereby cutting off fluid communication between the first channel 9 and the third channel 11.

There is no possibility for the incoming gas flow to bypass the occlusion provided by the portion 22, as the annular groove 24 is displaced so as to be off the flow path, and the portion 22 seals the entire bore of the channel 10. In this condition a fluid communication is established between the gas inlet 2 and the plenum PL of the accumulation chamber 5, thereby gas may be accumulated (with an increase in pressure) in the plenum PL of the chamber 5 by deformation of the membrane 15, which also allows a volume increase of the plenum PL.

Figure 6:
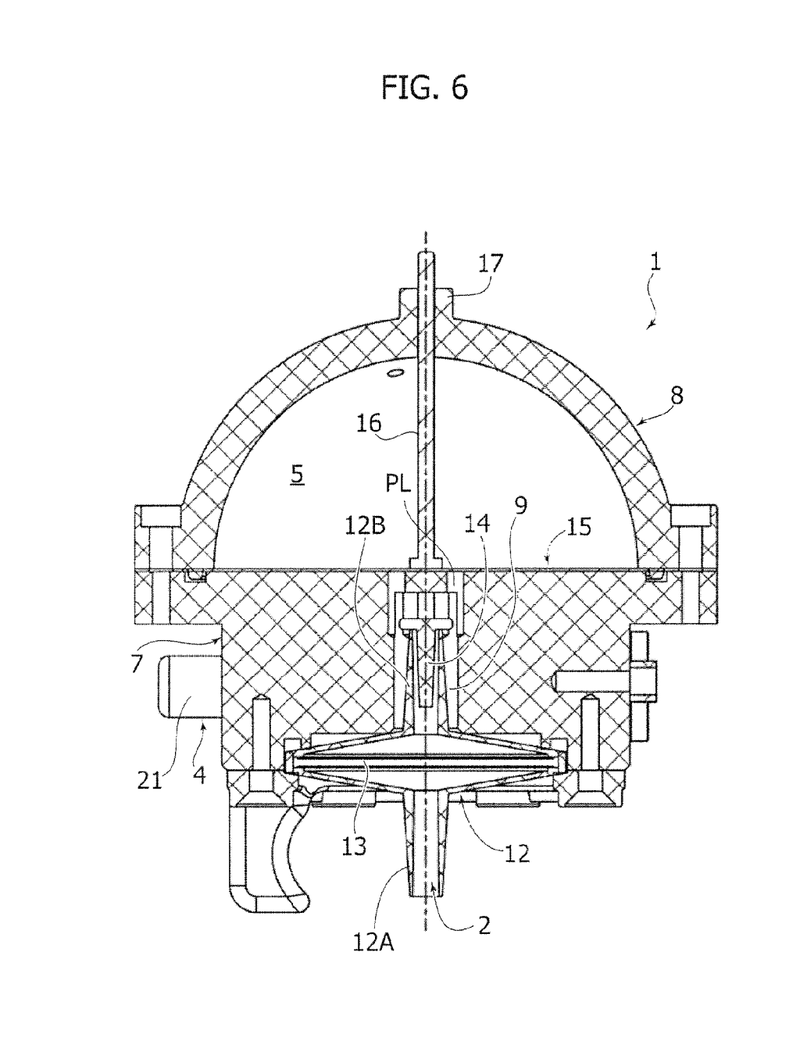
FIG. 6 illustrates an operating condition of the purger device, according to embodiments of the disclosure.
Figure 7:
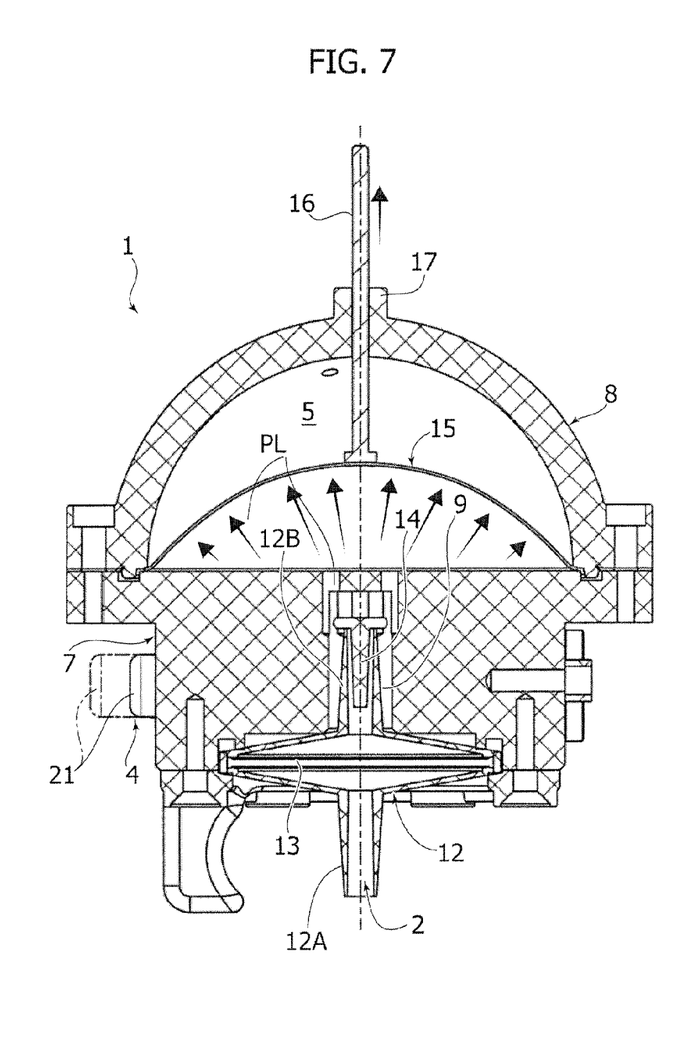
FIG. 7 illustrates an operating condition of the purger device, according to embodiments of the disclosure.

FIGS. 4 and 6 show the purger device 1 in the first operating condition of the flow control unit 4 (push button 21 in the first operating condition and undeformed membrane 15, while FIG. 7 shows the purger device 1 in the second operating condition of the flow control unit 4 (push button 21 in the second operating condition and deformed membrane 15).

Operation of the purger device 1 in embodiments herein will now be described with reference to FIG. 2.

Whenever a "wet lung" issue occurs that requires purging of the gas exchange hollow fibers, the perfusionist may resort to the purger device 1, and especially to the flow control means (spool valve) 4. In normal operation, the spool valve is in the first condition, i.e. a free flow of blended gas is allowed from the gas inlet to the gas outlet, which are in fluid communication. The perfusionist may resort to the purger device 1 to provide a short-duration pressure spike or surge in the gas exchange hollow fibers in the oxygenator OXY that removes condensed water vapor.

With reference to FIG. 7, this is done by (de)pressing the push button 21 into the main housing 7, thereby moving the spool member to a position that provides the second operating condition of the spool valve and varies the connection pattern between the ports of the purger device 1, namely by isolation of the gas inlet 2 from the gas outlet 3. Accordingly, blended gas from the gas blender GBL can only accumulate through the channel 9 into the plenum PL of the accumulation chamber 5, which expands in volume by deformation of the membrane 15, with a subsequent increase in pressure. The perfusionist may have visual evidence of the extent of gas accumulation in the plenum of chamber 5 by the gauge pin 16, which, in embodiments, may be graduated or color coded to provide additional reference to the perfusionist. Additionally, in embodiments the gauge pin 16 may be replaced by a position transducer coupled to the membrane and connected to a control unit with visual position indication, for example via colored LED lights (e.g. green for low accumulation, orange for medium accumulation, red for high accumulation). Yet further a pressure transducer can be built or embedded into the channel 9 to sense the pressure in the plenum of chamber 5 and output a visual indication thereof, again moderated by a control unit driving the LED light(s) as per the above.

The mobile spool member 18 may also be operated through an electric pilot stage, for example a touch button driving a solenoid actuator of the mobile spool member 18. In this latter case, an electronic control unit may be provided to control operation, as well as to implement certain control strategies such as whether solenoid operation has to be maintained as long as the touch button is pressed or whether it is initiated at the press of the button and maintained in the second operating condition.

In embodiments, purging of the gas exchanger hollow fibers experiencing wet lung phenomena may be achieved by returning the flow control means (spool valve 4) to the first operating condition. This may be done, in embodiments herein, by simple release of the push button 21 with return of the mobile spool member 18 to the resting position (shown in FIGS. 4 and 6) under the biasing action of the spring 20.

This restores fluid communication between the gas inlet 2 and the gas outlet 3, and—more relevantly—it also allows the pressurized gas in the plenum of chamber 5 to be vented through the very gas outlet 3. The one-way valve 14 prevents the pressure surge from being vented towards the gas inlet 2.

The sudden release of the pressurized gas from the accumulation chamber 5 urges the same through the feed line from the gas outlet 3 to the oxygenator, which in turn results in the condensed water vapor in the hollow fibers being flushed away through the oxygenator gas escape OX_OUT.

It is noted in this respect that purging may be operated by the perfusionist (or by the electronic control unit driving the solenoid actuator that operates the mobile spool member 18) either at pre-set intervals or on-demand. In this latter case, the provision of the gauge pin 16 offers visual evidence of pressure build up at the gas outlet 3 owing to reduced flow sections from water condensation. When in the first operating conditions, the porting of the accumulation chamber 5 downstream of the inlet channel 9, i.e., the porting of the plenum PL, and accordingly on the way to the outlet channel 11 and gas outlet 3, makes the plenum of the accumulation chamber sensitive to increases in blended gas delivery pressure at the gas outlet 3. Accordingly, even in normal operation the membrane 15 may sense pressure from the porting thereof and bulge into the dome 8, thus extracting the gauge pin proportionally to the pressure sensed through the port of the chamber 5. Accordingly, based on visual coding of the gauge pin the perfusionist may decide to operate purging of the oxygenator even before detecting wet lung conditions from, e.g., reduced exchange efficiency and/or poor blood oxygen delivery.

Pressure buildup into and release from the variable volume plenum PL is, in embodiments, particularly effective in that volume expansion during the loading of the plenum PL results in the storage of (pressure) energy within the plenum itself either by deformation of the elastic membrane or by displacement of a spring loaded piston. Such energy is later returned through the gas outlet 3 and the oxygenator essentially as a pressure pulse which performs the purging action when the flow control unit 4 is switched back to the first operating condition, e.g., by release of the push button 21.

In embodiments, the purging action is particularly effective as compared, for instance, to a fixed volume plenum which could not afford a significant energy storage based on typical perfusion gas pressures generally low to avoid blood embolization. Conversely, a variable volume plenum such as plenum PL may rely on volume expansion as a means for effective (and sufficient) energy storage and release.

The same purging strategy is of course available in case of an electrically operated spool valve and/or a pressure transducer sensing the pressure on the gas outlet 3 and driving visual communication means (e.g. the LED lights referred to in the foregoing) to give evidence of the pressure level on the gas outlet 3.

An electrically operated spool valve or flow control unit may be used, in embodiments, to run a predetermined purge cycle schedule, for example featuring purging cycles at predetermined time intervals (e.g. 30 minutes) or pressure threshold in chamber 5 for purge activation and a related alarm when such threshold is reached.

Yet further, the perfusion system may feature oxygen delivery measuring means and/or blood $CO_2$ concentration measuring means which may be used in combination with pre-set oxygen delivery threshold (minimum allowable oxygen delivery) and/or maximum $CO_2$ concentration threshold to either automatically perform a purge cycle, or to output an alarm signal or message informing the perfusionist that a purge cycle should be performed. Alarm signals or message may be used also with manually operated purger devices featuring the push button 21.

Moreover, the pressure at which the accumulation chamber loading stage is to be concluded may be set or controlled by the perfusionist. In fact, the perfusionist may decide a maximum amount of gauge pin 16 extraction from the dome 8 as maximum pressure reference for the release of the push button, or—alternatively if the gas pressure is measured by a sensor the perfusionist may set a maximum pressure value at which the loading stage should be concluded by automatically opening the gas outlet 3 to the oxygenator OXY.

Unlike prior art purging techniques and method, the purger device 1 is inherently safe in that the surge in pressure and gas flow from the sudden release of gas from the accumulation chamber 5 is sufficiently short in duration (a few seconds), and sufficiently limited in additional mass to avoid gaseous embolization of blood running across the hollow fibers.

Figure 8:
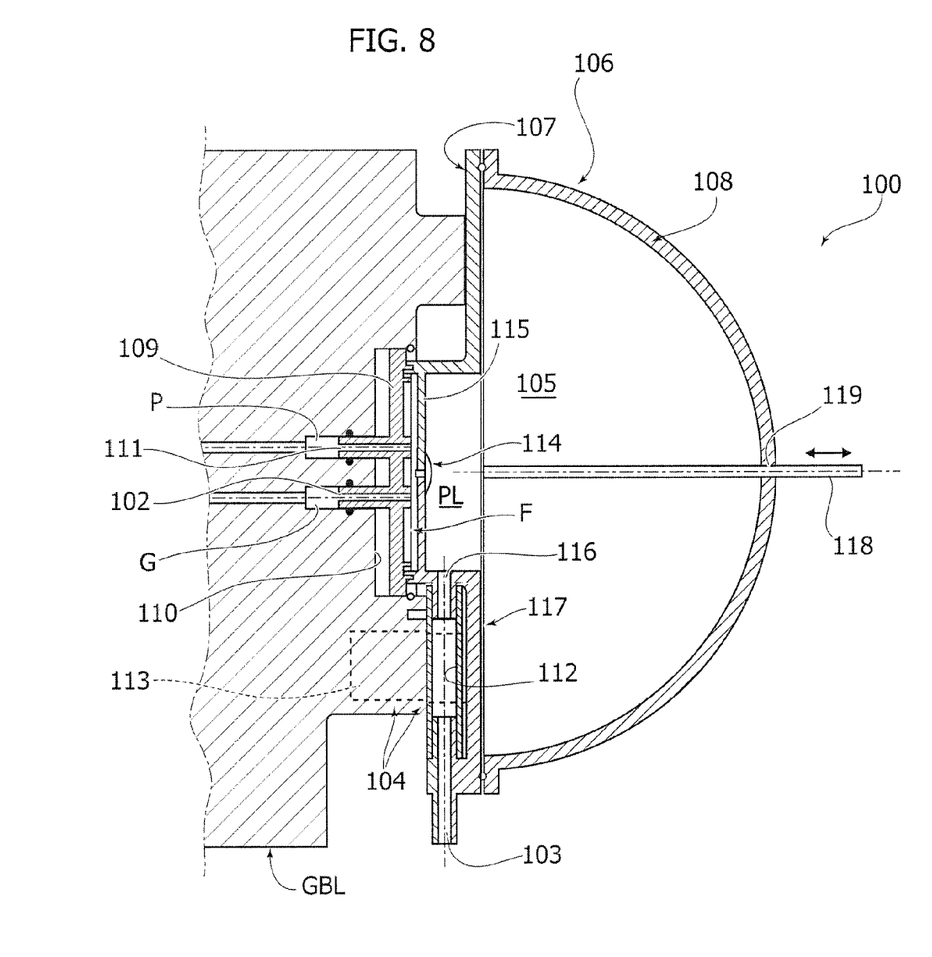
FIG. 8 shows a cross sectional view of a purger device, according to embodiments of the disclosure.

With reference to FIG. 8, embodiments of a purger device are designated as a whole by reference number 100. While the purger device 1 according to embodiments maybe suitable as a stand-alone device, the purger device 100 is suitable for integration with a gas blender GBL.

In embodiments, the purger device 100 includes a gas inlet 102, a gas outlet 103, a fluid communication feature between the gas inlet 102 and the gas outlet 103, a flow control unit 104 configured to vary fluid communication patterns in the fluid communication feature, and an accumulation chamber 105 including a plenum PL ported to the fluid communication feature so as to be in fluid communication with the gas inlet 102 and/or the gas outlet 103 depending on the fluid communication pattern established by the flow control unit 104.

Similarly to the purger device 1, the accumulation chamber 105 includes the plenum PL, which is an inner volume delimited by inner walls and boundaries of the accumulation chamber 105. The plenum PL is a variable volume plenum in that it is at least partly delimited by a deformable member, e.g., an elastic membrane, or a displaceable member, e.g., a spring biased piston, for instance in a cylinder shaped accumulation chamber, so to accommodate volume variations of the plenum itself.

In embodiments, the purger device 100 may include a casing 106 comprising a main housing 107 and a dome 108 fastened to the main housing 107.

In embodiments, the main housing 107 is further fastened to a backplate 109 which is provided as a connector interface to a receiving socket 110 of the gas blender GBL. The receiving socket 110 is configured to host the purger device 100, which can be plugged into the gas blender GBL as an add-on.

The backplate 109 may comprise a first tube connector defining the gas inlet 102 and plugged into a gas delivery line G of the gas blender GBL, and a second tube connector 111 defining a pressure sensing port for a pressure transducer (not shown) which may be used to assist with purging operations as described in the foregoing. The connector 111 is plugged into a pressure sensing line P of the gas blender GBL, wherein the pressure sensing line P may receive a built-in pressure transducer. The pressure transducer may alternatively be built into the purger 100, for example at a plenum PL of the chamber 105. The connector 111 is furthermore ported to the plenum PL.

In embodiments, the flow control unit 104 of the purger device 100 may be provided as clampable tube connection 112 having one end in fluid communication with the gas inlet 102, particularly the volume downstream of the latter, including the location at which the accumulation chamber 105 of the purger device 100 is ported to the fluid communication feature of the purger device 100. The other end of the clampable tube 112 is connected to the gas outlet 103.

A clamp member 113, in embodiments an electrically actuated clamp member, is arranged at the clampable tube 112 and is configured to selectively clamp and release the clampable tube 112 to vary the fluid communication pattern in the fluid communication feature.

In embodiments, porting of the plenum PL of the accumulation chamber 105 to the fluid communication feature of the purger device 100 may be provided through a one-way valve 114, in some embodiments mushroom (or umbrella) shaped, sitting on a divider plate 115 downstream of the gas inlet 102. The valve 114 is normally kept open when gas flows through the inlet 102. Additionally, a channel 116 may be provided in the main housing 107 connecting the plenum PL of the chamber 105 downstream of the valve 114 to the clampable tube 112. In embodiments, the plenum PL of the accumulation chamber 105 features a variable volume thanks to the provision of a membrane 117 (which is a deformable member within the meaning referred to above). The membrane 117 is fixed to the casing 107 along a perimeter thereof (e.g. pinched or nipped between the dome 108 and the main housing 107) and includes one side exposed to the plenum PL of the chamber 105 downstream of the gas inlet 102 (hence in view of the gas inlet 102), and the opposite side exposed to the interior of the dome 108, which caps the membrane 117.

The dome 108 has a substantially hemispherical shape to accommodate the bulging deformation of the membrane 117 when subject to gas pressure and flow from the gas inlet 102.

In embodiments, the clamp member 113 includes a first operating condition wherein no restriction (clamping) action is exerted on the clampable tube 112, so that a fluid communication is established between the gas inlet 102 and the gas outlet 103, while also maintaining fluid communication with the porting location of the plenum PL of the accumulation chamber 105. The clamp member 113 includes a second operating condition wherein a clamping action with flow occlusion of the gas outlet 103 and fluid communication kept between the gas inlet 102 and the plenum PL of the accumulation chamber 105 to feed the plenum PL with pressurized gas from the blender GBL, and cause the expansion of the membrane 117 into the dome 108.

In embodiments, the membrane 117 may be advantageously coupled to a gauge pin 118 mounted slidable through a hub 119 provided at the summit of the dome 108. The gauge pin 118 provides visual evidence of the membrane deformation, and accordingly the pressure level of the gas in the chamber 105.

An advantage of the gas purger 100 as compared with stand alone purgers such as the purger 1 may include the purger 100 being integrated with a gas filter, in that—for instance—a 0.2 μm gas filter (reference F in FIG. 8) is always used along the gas supply line connected to the gas inlet port of the oxygenator OXY, which makes it easier to set up the purger 100. Additionally, the purger 100 may allow designing the gas blender 100 in connection with the purger 100 in a way that the latter may be used by means of features included in the gas blender.

In operation, the gas supplied by the gas blender GBL from gas inlet 102 flows through the gas filter F and the one way valve 114 into the plenum PL of the chamber 105, ahead to the tube 112 and the gas outlet 103, and eventually to the gas inlet OX_IN of the oxygenator OXY. It is noted in this respect that the circuit layout of the perfusion system does not vary with respect to what described for the purger device 1.

In embodiments, gas pressure downstream the filter F may be measured by means of a pressure transducer (built into the gas blender GBL) and a sensing line from connector member 111.

The pressure sensed by the transducer substantially coincides with the pressure at the gas inlet OX_IN of the oxygenator, which in turn is sensitive to the amount of water condensation inside the hollow fibers of the oxygenator OXY, i.e., it increases as the amount of water condensation increases.

The perfusionist may at any time manually initiate a purging cycle by pressing a purge control on the gas blender GBL, which in embodiments may be provided as a push button on the gas blender GBL. The operation of the purge control may trigger the issue of a control signal which activates the electrically actuated clamp member 113 so as to clamp the tube clampable tube 112, thereby occluding the gas outlet 103 while maintaining fluid communication between the gas inlet 102 and the plenum PL of the accumulation chamber 105. This is made, i.e., by porting the plenum PL of the accumulation chamber 105 to the fluid communication feature of the purger device 100 upstream of the tube 112.

The clamping of the tube 112 provides a transition from the first operating condition of the flow control unit 104 (fluid communication between gas inlet 102 and gas outlet 103, with the plenum PL of the accumulation chamber 105 also in fluid communication therewith) to the second operating condition of the flow control unit 104 (cutoff of the gas outlet 103 and fluid communication maintained between gas inlet 102 and the plenum PL of the accumulation chamber 105), which in turn causes the elastic membrane 117 to deflect under the action of the gas inlet pressure and bulge into the dome 108.

Maximum deflection of the membrane 117 is determined by the dome 108, the walls of which limit the deformation of the membrane 117. The dome 108 may be sized and dimensioned to limit the deflection to a safe value, i.e., a value that does not result in too high of a pressure surge when venting the accumulation chamber to the oxygenator.

In embodiments, the duration of membrane 117 deflection may feature around a few seconds, and accordingly the pressure sensed by the transducer through connector member 111 progressively grows to a maximum value corresponding to the maximum allowed membrane 117 deflection (either determined by the walls of the dome 108 or by an adjustable pressure value).

The purge impulse to the oxygenator OXY may then be delivered by releasing the clamping action on the clampable tube 112 (which is provided by the clamp member 113), which restores free flow between the gas inlet 102 and the gas outlet 103 and vents the pressurized fluid in the plenum PL of the chamber 105 to the oxygenator gas inlet OX_IN. Purging occurs as detailed in the foregoing regarding the purger device 1: the elastic membrane 117 recovers the deformation and forces the accumulated air out through the gas outlet 103 and into the hollow fibers of the oxygenator OXY, thereby flushing condensed water vapor from the same through the gas escape OX_OUT.

Similarly to purger device 1, in the purger device 100 pressure buildup into and release from the variable volume plenum PL is, in embodiments, particularly effective in that volume expansion during the loading of the plenum PL results in the storage of (pressure) energy within the plenum itself either by deformation of the elastic membrane or by displacement of a spring loaded piston. Such energy is later returned through the gas outlet 103 and the oxygenator essentially as a pressure pulse which performs the purging action when the flow control unit 104 is switched back to the first operating condition (e.g. by release of the clampable tube 112).

In embodiments, the purging action is particularly effective as compared, for instance, to a fixed volume plenum which could not afford a significant energy storage based on typical perfusion gas pressures generally low to avoid blood embolization. Conversely, a variable volume plenum such as plenum PL may rely on volume expansion as a means for effective (and sufficient) energy storage and release.

In embodiments, the perfusionist may be provided with additional control options for initiating purging cycles. For example, in embodiments the gas blender GBL may be provided with an electronic control unit allowing for custom purge cycle settings, including e.g. maximum purge pressure, and/or purge timing, via control of the clamp member 113 and data feedback from the sensing line 111, P (or even from the oxygenator, as will be detailed in the following).

For example, in a fully automatic, time-based, mode the perfusionist may set up the gas blender GBL with integrated purger device 100 so that the purge cycle is initiated at preset time intervals, regardless of the loading pressure of the accumulation chamber 105 or the amount of backpressure generated by condensed water vapor amount in the oxygenator hollow fibers.

The fully automatic mode may envisage either a pure time-based control, or a mixed time- and pressure-based control. For example, in the pure time-based control the operation of the gas blender with integrated purger device only depends on timing of relevant cycle events, i.e., start of purger loading (SPL), purging pulse release (PPR end of loading), time to next start (TTS) of purger loading. In this case, purging cycles are initiated regardless of the amount of condensed water vapor inside the hollow fibers of the oxygenator, as the control strategy is not pressure-sensitive.

In other words, in the pure time-based control mode, the control unit is configured for:
  operating the clamp member 113 to occlude the clampable tube 112, thereby bringing the flow control unit 104 to the second operating condition and allowing gas to accumulate in the plenum PL of the accumulation chamber 105, at a first preset time (SPL); and operating the clamp member 113 to release the clampable tube 112, thereby bringing the flow control unit 104 (back) to the first operating condition and venting the gas accumulated in the accumulation chamber through the gas outlet 103 of the purger device 100, at a second preset time (PPR), the second preset time being later than the first preset time.

In the mixed time- and pressure-based control the perfusionist may additionally set up the gas blender GBL so that the purge cycle in the oxygenator is initiated:
  a) when a predetermined backpressure threshold at the gas outlet 103 (i.e. a backpressure from the oxygenator gas inlet is reached; the primary controlled variable is SPL; and
  b) when a predetermined backpressure threshold at the purger device gas outlet 103 is reached and/or when a predetermined loading pressure is reached in the plenum PL of the chamber 105; the controlled variables are SPL and/or PPR.

In the control strategy according to a), an electronic control unit onboard the gas blender GBL may automatically adjust timing of SPL, TTS by feeding back pressure information from the sensing line 111, p when the flow control unit is in the first condition (tube 112 not clamped), i.e., on the basis of backpressure amount at the gas outlet 103 (from the oxygenator OXY gas inlet). In-cycle phase shift between PPR and SPL may be chosen to be constant, so that the pressure of the gas in the plenum PL of the chamber 105 at the end of loading may in principle be subject to small variations. SPL timing (and TTS) accordingly may be adjusted to compensate for higher than expected condensed water vapor buildup in the hollow fibers lumen in the oxygenator, or lower than expected condensed water vapor buildup in the hollow fibers lumen in the oxygenator.

In the control strategy according to b), an electronic control unit onboard the gas blender GBL may automatically adjust timing of SPL, PPR, TTS by feeding back pressure information from the sensing line 111 when the flow control unit is in the first condition (tube 112 not clamped) and when the flow control unit is in the second condition (tube 112 clamped), i.e., based on either of (or both) the basis of backpressure at the gas outlet 103 from the oxygenator OXY, and loading pressure in the chamber 105.

Because the sensing line 111 remains exposed to the plenum PL of chamber 105 regardless of the operating condition of the flow control unit 104 (tube 112 clamped/not clamped), pressure feedback from the same may be used as an input variable throughout all the stages of the working cycle. For example, when the tube 112 is unclamped, pressure feedback from line 111 may trigger a correction of SPL timing by the control unit to compensate for the oxygenator backpressure and initiate loading of the purger 100 (i.e. loading of the plenum PL of chamber 105) earlier or later depending on the needs. When it is determined that loading of the plenum PL of chamber 105 is to be initiated, the sensing line 111, P immediately become sensitive to the pressure buildup in the chamber itself as the gas outlet 103 is cut off. Accordingly, the control unit may react by shifting PPR timing based on the maximum loading pressure desired by the perfusionist. Once the purging pulse is released by unclamping the tube 112 (releasing clamping action by the clamp member 113 via control signal from the control unit), TTS (next SPL) timing may be once again dynamically adjusted based on pressure feedback from the oxygenator, as following PPR the sensing line 111 returns to be sensitive to backpressure from the oxygenator OXY.

It is also to be noted that in some cases control strategies featuring gas outlet 103/oxygenator gas inlet backpressure feedback (a) and (b) for instance may be implemented replacing the backpressure feedback with an delivery feedback. Oxygen delivered to the extracorporeally circulating blood provides evidence of water vapor condensation in the oxygenator. Therefore, if the oxygen delivery value decreases below a certain threshold, this may be due to a gas exchange process in the oxygenator negatively altered by excessive water condensation and thus may be taken as an indicator that a purging cycle needs to be executed.

Moreover, the oxygen delivery-based control may be integrated with back pressure control for redundancy reasons and consistency check. In one embodiment, pressure from the sensing line 111 may be the main control variable, while oxygen delivery may be the redundant/consistency-testing control variable. When pressure feedback from line 111 provides evidence of backpressure from the oxygenator exceeding a preset threshold, a consistency check may immediately be performed by the control unit by retrieving the oxygen delivery information. If the latter exhibits the expected correlation with the sensed backpressure (raising back pressure, reduced oxygen delivery), the feedback signal may be confirmed for consistency and switching of the flow control unit 104 to the second condition may be initiated.

In a semi-automatic, pressure-based, operation mode, the gas blender GBL may be manually operated by the user to initiate (via the control unit) the clamping action on the clampable tube 112 (manual SPL), while the clamping action may be automatically released by the control unit upon reaching of a predetermined loading pressure (automatic PPR).

In other words, in this control mode the control unit is configured for:

operating the clamp member 113 to occlude the clampable tube 112, thereby bringing the flow control unit to the second operating condition and allowing gas to accumulate in the accumulation chamber 105 in response to a manual control initiated by a user (e.g. the perfusionist), and operating the clamp member to release the clampable tube 112, thereby bringing the flow control unit to the first operating condition and venting the gas accumulated in the accumulation chamber through the gas outlet 103 of the purger device 100, when a threshold pressure in the plenum PL of said accumulation chamber 105 is reached or exceeded.

The longer the preset deflection/chamber loading duration (or the higher the deflection pressure), the more vigorous is the purging pulse. Accordingly, setting the deflection/chamber loading duration (or pressure) may be regarded as a way to adjust the pulse strength.

Another possibility for semi-automatic control envisages the use of gas outlet 103/oxygenator backpressure as a control variable. The perfusionist may be presented with a visual or audio alarm whenever a backpressure threshold is exceeded. Moreover, in all of the control strategy disclosed herein—regardless of whether in fully-automatic or semi-automatic operation—visual or audio alarms may be delivered to the perfusionist to indicate that the threshold concerned (backpressure, loading pressure, oxygen delivery) has been reached. In semi-automatic mode, the alarm may be used to trigger manual purging by the perfusionist.

While the principles of the disclosure remain the same, the details of construction and the embodiments may widely vary with respect to what has been described and illustrated purely by way of example, without departing from the scope of the present disclosure.

What is claimed is:

1. A purger device for hollow fiber oxygenators, including:
    a gas inlet;
    a gas outlet; and
    a fluid communication feature between said gas inlet and said gas outlet;
the purger device further including:
    an accumulation chamber having a variable volume plenum ported to said fluid communication feature; and
    a flow control unit configured to vary fluid communication patterns in said fluid communication feature and having a first operating condition and a second operating condition,
    wherein in the first operating condition the flow control unit enables a fluid communication between said gas inlet and gas outlet, and wherein in the second operating condition the flow control unit enables a fluid communication between said gas inlet and the variable volume plenum of said accumulation chamber.

2. The purger device according to claim 1, wherein in the first operating condition said fluid accumulation chamber is maintained in fluid communication with the gas inlet and the gas outlet.

3. The purger device according to claim 1, wherein in the second operating condition said gas outlet is excluded from fluid communication between the gas inlet and the variable volume plenum of said accumulation chamber.

4. The purger device of claim 3, wherein in the second operating condition of the flow control unit the gas outlet is occluded.

5. The purger device of claim 1, wherein the variable volume plenum of said accumulation chamber is at least partly delimited by an elastic membrane configured for allowing volume expansion of said variable volume plenum when the flow control unit is in the second operating condition.

6. The purger device of claim 5, wherein said membrane is coupled to a gauge pin configured to protrude out of a casing of said purger device by an extent dependent on a deformation of said membrane.

7. The purger device of claim 6, wherein said membrane is capped by a dome, the gauge pin being mounted slidable through a hub provided on said dome.

8. The purger device of claim 1, wherein said flow control unit is a spool valve including a mobile spool member movable along a portion of said fluid communication feature.

9. The purger device of claim 8, wherein the mobile spool member is operable by way of a push button.

10. The purger device of claim 9, wherein the push button is biased towards the first operating condition.

11. The purger device of claim 8, wherein the mobile spool member is electrically operated.

12. The purger device of claim 8, including a main housing comprising:
    a first, inlet, channel having a first axis, the first channel being in fluid communication with the gas inlet;
    a second channel having a second axis orthogonal to the first axis; and
    a third, outlet, channel having a third axis orthogonal to the first axis and the second axis, the third channel being in fluid communication with the gas outlet, and wherein the mobile spool member is arranged slidable along the second channel.

13. The purger device of claim 12, wherein the mobile spool member includes a first portion and a second portion separated by an annular groove,
    wherein in the first operating condition the mobile spool member is positioned such that the annular groove is in view of the first channel and the third channel to allow a fluid flow through the fluid communication feature to bypass the spool member when proceeding from the gas inlet, through the first channel, and out to the gas outlet.

14. The purger device of claim 13, wherein in the second operating condition the mobile spool member is positioned so that the first portion overlaps with a porting of the first channel onto the second channel and with a porting of the third channel onto the second channel, thereby cutting off fluid communication between the first channel and the third channel.

15. The purger device of claim 1, wherein the flow control unit includes a clampable tube providing the gas outlet, and an electrically operated clamp configured to selectively clamp or release the clampable tube.

16. The purger device of claim 15, including a backplate provided with said gas inlet, the backplate being configured for fitting the purger device into a receiving socket of a gas blender.

17. The purger device of claim 16, wherein said backplate also includes a connector member providing a pressure sensing line.

18. The purger device of claim 1, wherein said gas inlet is in fluid communication with said variable volume plenum of said accumulation chamber.

19. The purger device of claim 18, wherein said connector member providing the pressure sensing line is in fluid communication with said variable volume plenum.

20. The purger device of claim 18, wherein a one-way valve is arranged between said variable volume plenum and said backplate.

21. The purger device of claim 18, wherein said clampable tube is in fluid communication with said variable volume plenum.

22. A gas blender for use in a perfusion system, the gas blender comprising a receiving socket and a purger device according to claim 16 hosted in said receiving socket.

23. The gas blender of claim 22, including a blended gas delivery port and a pressure sensing port, and wherein the backplate of said purger device includes:
 a first connector member providing said gas inlet; and
 a second connector member ported to the fluid communication feature of said purger device,
 wherein the first connector member is configured to plug into the gas delivery port when the purger device is fitted into the receiving socket, and
 wherein the second connector member is configured to plug into the pressure sensing port when the purger device is fitted into the receiving socket.

24. The gas blender of claim 23, further including a pressure transducer configured for sensing pressure in the fluid communication feature of the purger device through said pressure sensing port and said second connector member, the pressure transducer being operatively connected to a control unit configured for operating a clamp member to selectively occlude the clampable tube at the gas outlet of the purger device.

25. The gas blender of claim 24, wherein the control unit is configured for:
 operating the clamp member to occlude the clampable tube, thereby bringing the flow control unit to the second operating condition and allowing gas to accumulate in the variable volume plenum accumulation chamber, when a first threshold pressure is reached or exceeded and sensed by the pressure transducer, the threshold pressure being a threshold backpressure at the gas outlet of the purger device; and
 operating the clamp member to release the clampable tube, thereby bringing the flow control unit to the first operating condition and venting the gas accumulated in the variable volume plenum of the accumulation chamber through the gas outlet of the purger device, when a second threshold pressure is reached or exceeded, the second threshold pressure being a threshold pressure in said variable volume plenum of the accumulation chamber.

26. The gas blender of claim 24, wherein the control unit is configured for:
 operating the clamp member to occlude the clampable tube, thereby bringing the flow control unit to the second operating condition and allowing gas to accumulate in the variable volume plenum of the plenum of the accumulation chamber in response to a manual control initiated by a user; and
 operating the clamp member to release the clampable tube, thereby bringing the flow control unit to the first operating condition and venting the gas accumulated in the variable volume plenum of the accumulation chamber through the gas outlet of the purger device, when a threshold pressure in said accumulation chamber is reached or exceeded.

27. The gas blender of claim 24, wherein the control unit is configured for:
 operating the clamp member to occlude the clampable tube, thereby bringing the flow control unit to the second operating condition and allowing gas to accumulate in the variable volume plenum of the accumulation chamber, at a first preset time; and
 operating the clamp member to release the clampable tube, thereby bringing the flow control unit to the first operating condition and venting the gas accumulated in the variable volume plenum of the accumulation chamber through the gas outlet of the purger device, at a second preset time, the second preset time being later than the first preset time.

28. A method of purging gas exchange hollow fibers of a blood oxygenator in a perfusion system by means of a purger device according to claim 1,
 wherein the gas exchange hollow fibers include inner lumens in fluid communication with an oxygenator gas inlet,
 wherein the perfusion system includes a gas blender configured to deliver a gas blend to the gas inlet of said purger device, and
 wherein the gas outlet of the purger device is in fluid communication with the oxygenator gas inlet,
 the method comprising:
switching the flow control unit to the second operating condition to accumulate gas from the gas blender in the variable volume plenum of the accumulation chamber; and
 switching the flow control unit to the first operating condition to release the gas accumulated in the variable volume plenum of the accumulation chamber to the oxygenator gas inlet, thereby flushing the inner lumens of the gas exchange hollow fibers.

29. The method of claim 28, wherein
 said switching the flow control unit to the second operating condition is performed at a first preset time; and
 said switching the flow control unit to the first operating conditions is performed at a second preset time, later than the first preset time.

30. The method of claim 29, further comprising estimating whether an accumulation of condensed water vapor in the inner lumens of the gas exchange hollow fibers exceeds a predetermined threshold,
 wherein said switching the flow control unit to the second operating condition is performed upon exceeding said predetermined threshold.

31. The method of claim 30, wherein said predetermined threshold is a first threshold pressure, the first threshold pressure being a threshold backpressure at the gas outlet of the purger device.

32. The method of claim 30, wherein said predetermined threshold is a minimum allowed oxygen delivery threshold to a patient's blood flowing across the gas exchange hollow fibers.

33. The method of claim 30, wherein said switching the flow control unit to the first operating condition is performed when gas pressure in the variable volume plenum of the accumulation chamber exceeds a second pressure threshold, the second pressure threshold being a pressure threshold in the variable volume plenum of the accumulation chamber.

34. The method of claim 29, wherein backpressure at the gas outlet of the purger device and/or gas pressure in the variable volume plenum of the accumulation chamber are fed back to a control unit to respectively adjust the timing of said switching the flow control unit to the second operating condition and/or switching the flow control unit to the first operating condition.

* * * * *